United States Patent [19]

Hanson et al.

[11] 4,276,658
[45] Jul. 7, 1981

[54] HEART VALVE PROSTHESIS

[75] Inventors: Donald W. Hanson; William E. Palmquist, both of Northfield, Minn.

[73] Assignee: St. Jude Medical, Inc., St. Paul, Minn.

[21] Appl. No.: 119,528

[22] Filed: Feb. 7, 1980

Related U.S. Application Data

[63] Continuation of Ser. No. 847,780, Nov. 2, 1977, abandoned.

[51] Int. Cl.³ .............................................. A61F 1/22
[52] U.S. Cl. .................................... 3/1.5; 137/512.1; 137/527.8
[58] Field of Search ..................... 3/1.5, 1; 137/512.1, 137/527, 527.8

[56] References Cited

U.S. PATENT DOCUMENTS

| 3,546,711 | 12/1970 | Bokros | 3/1.5 |
| 3,835,475 | 9/1974 | Child | 3/1.5 |
| 4,078,268 | 3/1978 | Possis | 3/1.5 |
| 4,114,202 | 9/1978 | Roy et al. | 3/1.5 |
| 4,159,543 | 7/1979 | Carpentier | 3/1.5 |

Primary Examiner—Ronald L. Frinks
Attorney, Agent, or Firm—Orrin M. Haugen; Thomas J. Nikolai

[57] ABSTRACT

A heart valve prosthesis coated in its entirety with pyrolytic carbon. In a preferred embodiment, the prosthesis is formed of a base having a blood passageway and dual leaflets pivotally secured to the base to regulate the flow of blood through the passageway. The pivot connection between the base and leaflets is formed by recesses in the base and projections on the leaflets, the recesses and projection termini being formed as surfaces of revolution. The valve is assembled by elastically deforming the base to allow insertion of the projections within the recesses.

16 Claims, 7 Drawing Figures

HEART VALVE PROSTHESIS

This is a continuation of application Ser. No. 847,780, filed Nov. 2, 1977, abandoned.

BACKGROUND OF THE INVENTION

Heart valve prostheses are known to the prior art. Essentially, such prostheses are formed of a base member having a blood passageway, means for securing the base member in position, and a valving member for controlling the flow of blood through the passageway. Typical valving members found in prior art heart valve prostheses include an occluder in the form of balls, leaflets or discs with each employing some form of retaining means to maintain the occluder in an operative relation to the passageway while allowing the occluder to move between open and closed positions to control blood flow. The retaining means have taken the form of hinge pins, cages, and projections from the base.

The deficiencies of many prior art heart valve prostheses reside in the occluder and/or the occluder retaining means. For example, a particular design may impose mechanical requirements on the retaining means necessitating the use of a material having characteristics inferior to those of another available material. Other deficiencies of prior art heart valve prostheses include inordinate size which limits their application, undesirable effects on the blood flow, localized sites of wear and fatigue, and regions of blood stagnation.

As indicated above, the material from which a heart valve prosthesis is fabricated may have a critical impact on the clinical applicability of that prosthesis. For example, pyrolytic carbon has been recognized as inert and thrombo-resistant in the body environment, and, as such, is ideal for use in prosthetic devices. However, most prior art prosthetic heart valve designs impose mechanical requirements in at least some of the elements which has prevented fabrication of the totality of the prostheses from pyrolytic carbon. A typical disc valve, for example, employs projections which engage the disc to maintain its position, the projections being deformed to accept the disc during assembly of the valve. In such a valve, the disc has been fabricated of pyrolytic carbon, but the base and projections have been formed of other materials capable of withstanding the required deformation. Alternatively, it has been suggested that the base be formed of a plurality of members which are secured to each other on assembly of the valve thereby eliminating the necessity to deform the retaining means for the occluder. This approach however, has not met with success possibly as a result of the potential for separation of the members as well as the potential for creating areas of blood stagnation. Also, the joint area of such a multi-member base prosthesis is not pyrolytic carbon. Pyrolytic carbon is coated on a substrate in a manner which is fully disclosed in U.S. Pat. No. 3,526,005, which is hereby incorporated by reference.

SUMMARY OF THE PRESENT INVENTION

The present invention provides a heart valve prosthesis whose exposed surfaces are coated in their entirety by pyrolytic carbon. The base is a unitary structure and includes means for retaining the occluder in position while allowing movement thereof between open and closed positions. In a preferred embodiment, the occluder is formed of two leaflets, both entirely coated with pyrolytic carbon, having projections which engage the retaining means of the base. The retaining means include stops to control the movement of the leaflets while the retaining means and leaflet projections cooperate to prevent blood stagnation in their area of engagement. In addition, the heart valve prosthesis of the present invention has a low structural profile relative to many prior art prostheses, a low pressure gradient resulting in a high efficiency, a minimal damaging effect on red blood cells, and results in a blood flow pattern superior to many prior art valves.

DETAILED DESCRIPTION OF THE DRAWINGS

Figure 1:
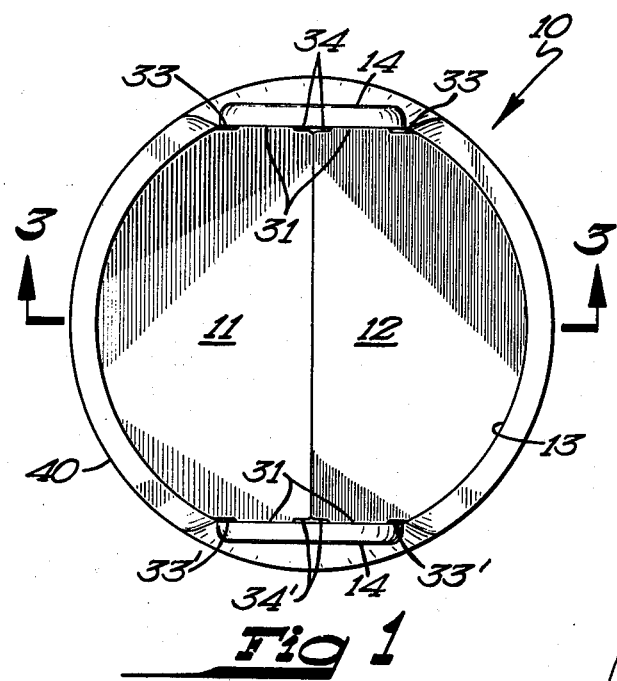
FIG. 1 is an upstream view of a preferred embodiment of the present invention with the occluder in a closed position.
Figure 2:
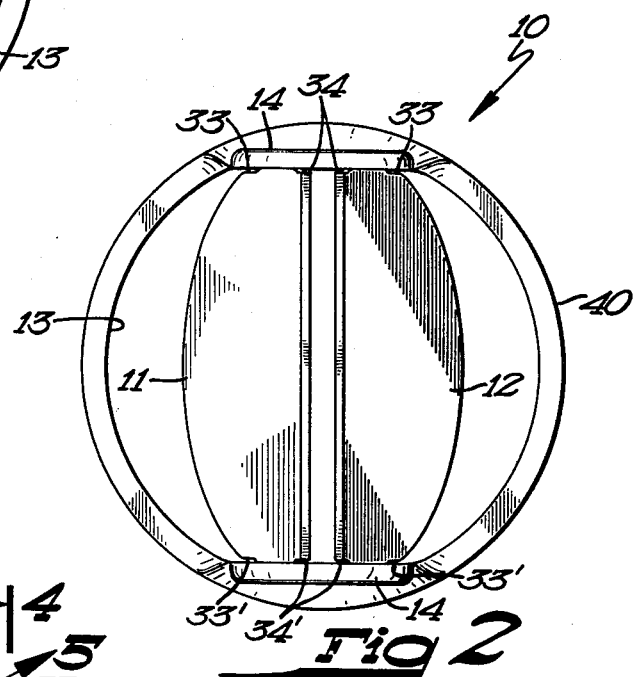
FIG. 2 is an upstream view of the embodiment of FIG. 1 with the occluder in an open position.

Referring now to FIG. 1, there is shown a preferred embodiment of the present invention formed of a base 10 and leaflets 11 and 12. The base 10 is a generally annular member whose inner wall 13 defines the blood passageway. The blood passageway is alternately opened (see FIG. 2) and closed by movement of the leaflets 11 and 12 in response to the flow of blood. As will be described more fully below, the base is provided with projections 14 having retaining means which cooperate with ears carried by the leaflets 11 and 12 to allow a pivotal movement of the leaflets between the positions illustrated in FIG. 1 and FIG. 2.

Figure 3:
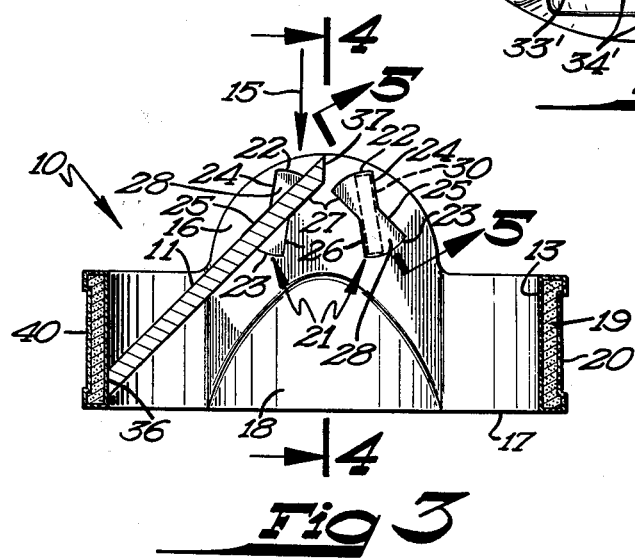
FIG. 3 is a cross-section taken along the line 3—3 in FIG. 1.
Figure 4:
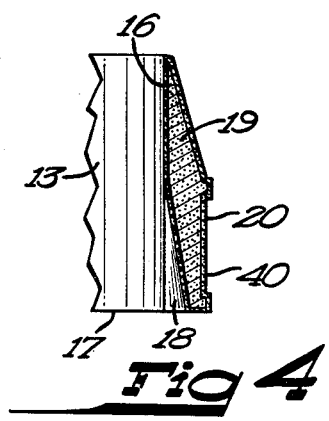
FIG. 4 is a cross-section taken along the line 4—4 in FIG. 3.

Referring now to FIG. 3, there is shown a cross-section taken along the line 3—3 in FIG. 1 with the leaflet 12 eliminated for purposes of illustration. The arrow 15 indicates the desired blood flow direction. As illustrated in FIG. 3, the projection 14 extends from the annular portion of base 10 in the upstream direction. The inner face of the projection 14 is provided with a flat portion 16 while the outlet or downstream terminus 17 of base 10 is generally circular, the portion 18 providing a transition between the circular configuration of the outlet 17 and the flat portion 16. As is known in the prior art, pyrolytic carbon is coated on a substrate, the reference numeral 19 indicating the substrate throughout the figures while the pyrolytic carbon coating is indicated at 20. The fabrication of the substrate and the coating of the pyrolytic carbon to the desired configuration are known to the prior art.

Flat portion 16 of projection 14 is provided with retaining means generally designated at 21. The retaining means 21 are formed as recesses within the flat 16 having opposing arcuate ends 22 and 23 joined by side walls 24–27, to form a bearing surface 28. As will be discussed more fully below, bearing surface 28 is a surface of revolution and preferably a spherical polygon.

Except for their orientation within the flat 16, the retaining means 21 are identical.

The recesses which form the retaining means 21 may be formed by a cylindrical grinding wheel having the diameter desired for the bearing surface 28 by feeding the grinding wheel into the flat 16 to the desired depth thereby forming the side walls 24 and 26. Such a grinding wheel is illustrated in phantom at 30 in FIG. 3. The grinding wheel may then be swept through the arc defined by the ends 22–23 to form the bearing surface 28 and the side walls 25 and 27. As will be described more fully below, leaflets 11 and 12 are provided with ears which are adapted to extend into the recesses forming retaining means 21 for pivotal movement therein. Any or all of the side walls 24–27 may be adapted to serve as stops for the leaflets 11 and 12 as by limiting motion of the leaflet ears within the retaining means 21. That is, as illustrated in FIG. 3, the side walls 25 and/or 27 may be positioned to prevent movement of the leaflet 11 past the illustrated position. Of course, an additional stop in the closed position may be provided by engagement of the leaflet 11 with the inner face 13 of base 10 as further illustrated in FIG. 3. At least one of side walls 24 and 26 serve as a stop for the occluders 11 and 12 in the open position.

Figure 5:
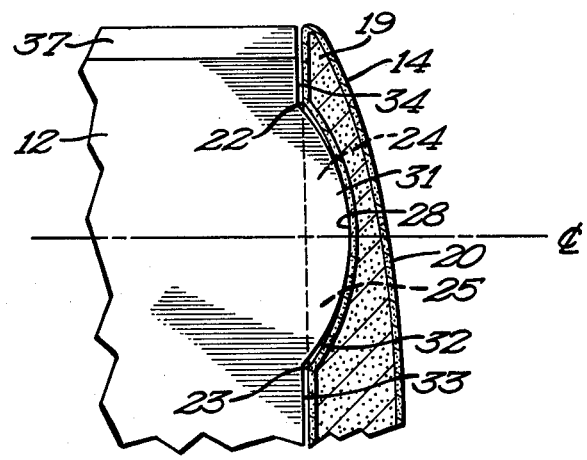
FIG. 5 is a cross-section taken along the line 5—5 in FIG. 3.

The configuration of the surface 28 and its cooperation with the described projection or ear of the leaflets 11 and 12 is illustrated in FIG. 5 which is a cross-section taken along the line 5—5 in FIG. 3. In FIG. 5, the leaflet 12 is partially illustrated including a circular projection of ear 31. The perimeter or terminus of the ear 31 is shaped as the section of a sphere having a diameter closely approximating but slightly smaller than, the diameter of the surface 28. In this manner, portions of the perimeter of ear 31 engage surface 28 during movement of the occluders 11 and 12 between the open and closed position to maintain the occluders in position while the potential for wedging is reduced. For the purposes of this specification, and the appended claims, this relationship between the ear 31 terminus and the bearing surface 28 is referred to as "compatible".

Figure 6:
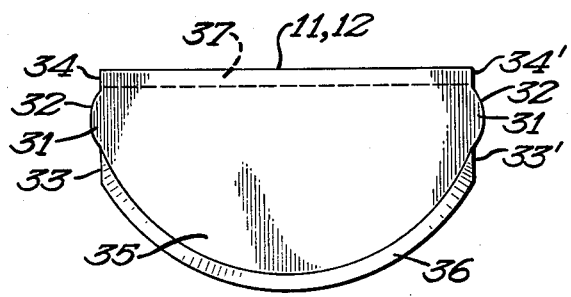
FIG. 6 illustrates a portion of the preferred embodiment of FIG. 1.

Referring now to FIG. 6, there is shown a preferred embodiment of the leaflets 11 and 12 which may be identical to each other. As described with reference to FIG. 5, the leaflets have an off-center pivot point in the form of a circular projection or ear 31 whose terminus 32 is a spherical polygon. Ears 31 lie between flat portions 33, 33' and 34, 34' which are adapted to lie adjacent to and cooperate with the flat 16 on projections 14. Arcuate portion 35 has a surface 36 which will abut against the inner wall 13 when the leaflets are in a closed position (See FIG. 3), while the surface 37 on each leaflet cooperates with the corresponding surface on the other leaflet in the closed position. The distances between the flat surfaces 33 and 34 and the primed flat surface of the same reference numeral are approximately the distance between the flat portions 16 of projections 14 such that when the ears 31 are within the retaining means 21 the leaflets are securely held in position. In a preferred embodiment, the ears 31 extend from their associated flat portions 33, 33', 34 and 34' by a distance less than the maximum depth of bearing surface 28, the flat portions 33, 33', 34 and 34' thereby cooperating with the flats 16 to prevent contact between the surface 28 and ear terminus 32 along the center line illustrated in FIG. 5. This further reduces the potential for wedging.

Figure 7:
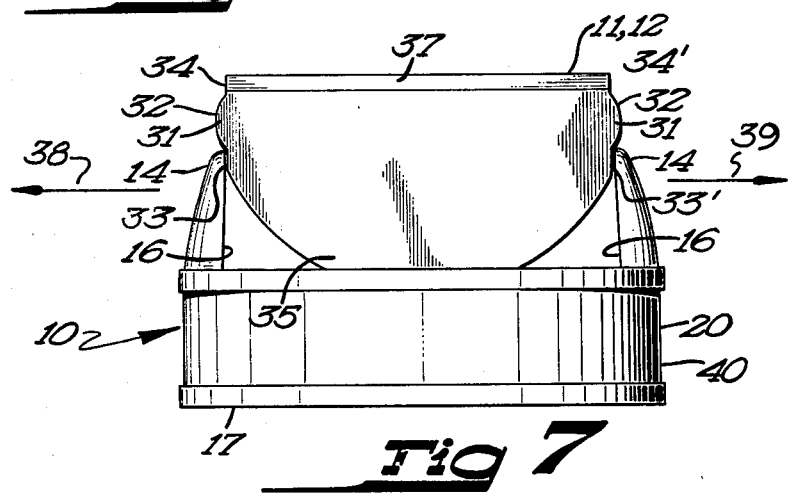
FIG. 7 illustrates the assembly of the preferred embodiment of FIG. 1.

Having described the various elements forming a part of the present invention, attention will now be directed to FIG. 7 and the method of assembly. It is uniformly accepted that pyrolytic carbon has greater structural strength in compressive stress than under tensile stress (see U.S. Pat. No. 3,676,179, which is hereby incorporated by reference). Accordingly, it has been assumed that any tensile deflection or deformation of a pyrolytic carbon element of a magnitude sufficient to accomplish any useful result would result in the destruction of that element. However, we have found that pyrolytic carbon can be elastically deformed sufficiently for the assembly of our valve. As described above, the surfaces 33 and 34 are spaced from the primed surfaces of like reference numerals by an amount approximating the distance between the surfaces 16 of the projections 14. Accordingly, the ears 31 cannot be positioned within the retaining means 21 of the flats 16 without the deflection of one or both of the projections 14 in the direction indicated by the arrows 38 and 39. Alternatively, the entirety of the main body 10 may be deflected, the projections 14 being deflected therewith. The assembly of the valve may be facilitated by placing one of the ears 31 within one of the retaining means 21 thereby reducing the amount of necessary deflection to approximate the amount of extension of the other ear 31 from the flat portions 33 and 34.

Larger valves that we have built and tested have required a deflection of 25 mils which we have accomplished repeatedly without deleterious effect on the valve assembly. In this process, the substrate 19 has typically been graphite. We have found that the thinner the graphite substrate, the greater the flexibility for a given thickness of pyrolytic carbon coating. For a given graphite thickness, there is an ideal coating thickness for maximum allowable deflection of the assembly. Above and below that ideal coating thickness, the allowable strain in the assembly decreases. The selection of substrate and coating thickness is within the skill of one ordinarily skilled in the art.

The present invention provides a prosthetic heart valve coated in its entirety with pyrolytic carbon without resort to multiple member base assemblies. The advantages resulting from the use of this thromboresistant material and the single piece construction of the valve base are believed obvious. Additionally, the physical characteristics of pyrolytic carbon from the standpoint of strength and wear result in a highly desirable valve. With reference to the illustrated embodiment, the dual of bi-leaflet configuration having a central opening greatly ameliorates the problems resulting from turbulence, regurgitation and eddy currents productd by several prior art valves.

The use of a leaflet having an off-center pivot point to respond to changes in flow direction is known to the prior art. However, we believe that the present invention accomplishes the desired attributes of such a valve without the attending complications of the retaining means of the prior art. For example, it has been suggested in the prior art to use hinge pins to engage a recess within the body. However, such a connection results in an area of potential blood stagnation with potential clotting consequences. Within the illustrated embodiment, movement of the valving members between the open and closed position causes the ears 31 to sweep through the recesses of the retaining means 21 to wipe or flush them out and eliminate, or at least greatly reduce, the stagnation problems of prior art pivot type connections. The compatible relationship between the ear terminus and bearing surface greatly enhances this wiping action. Such a compatible relationship may be attained with any configuration. A surface of revolution, however, is preferred and a spherical configuration most preferred.

Obviously, many modifications, and variations of the present invention are possible in light of the above teachings. For example, the assembly methods illustrated herein may be adapted to valves having a number of leaflets different from two or to leaflets of different configuration. Also, the projections 14 may be configured other than as illustrated. It is a portion of the present invention, however, to employ projections 14 that extend sufficiently around the annular portion 10 to shield the leaflets in the closed position so as to prevent radial leakage. The opening and closing angles of the leaves relative to the flow axis are easily determinable by one of ordinary skill in the art. We have found that a slight angular orientation of the leaves in the open position relative to the flow axis decreases their closing time and the associated regurgitation than would be the case if they were allowed to open fully. We presently contemplate an opening angle of 5°. Sizing of the valve assembly and its various components, as well as tolerances therein, to provide adequate one-way valve operation—with a limited retrograde or reverse flow to provide a constant washing action and motion—are easily determinable by a person of ordinary skill in the art. Additionally, securement of the valve assembly in position may be accomplished in any known manner, provision being made for a suturing ring in a groove 40 on the outer surface of body member 10, in known manner.

It is therefore to be understood, that within the scope of the appended claims, the invention may be practiced otherwise than as specifically described.

What is claimed is:

1. In a heart valve prosthesis of the type having base means including a blood passageway, means for regulating the flow of blood through the passageway and means for maintaining the regulating means in operative relation to the passageway, the improvement wherein said maintaining means comprises:
   (a) recess means within said base means, said recess means having a concave bearing surface formed as a substantially continuous surface of revolution; and
   (b) said regulating means comprising at least one leaflet having means projecting from the edge thereof and into said recess means, said projecting means being formed as a surface of revolution means about an axis normal to the plane of said leaflet and compatible with said concave bearing surface for forcibly flushing blood from said recess means upon operative movement of the projecting means of said leaflet within said recess means.

2. The prosthesis of claim 1 wherein said concave bearing surface and the termini of said projecting means are spherical.

3. In a heart valve prosthesis of the type having base means including a blood passageway, means for regulating the flow of blood through the passageway and means for maintaining the regulating means in operative relation to the passageway, the improvement wherein said maintaining means comprises:
   (a) recess means within said base means, said recess means having a bearing surface formed as a spherical polygon; and
   (b) means projecting from said regulating means into said recess means, the termini of said projecting means being formed as a surface of revolution means compatible with said bearing surface for flushing said recess means.

4. In a heart valve prosthesis of the type having base means including a blood passageway, means for regulating the flow of blood through the passageway and pivot means for maintaining the regulating means in operative relation to the passageway while allowing the regulating means to pivot, under the influence of the blood flow in said passageway, between open and closed positions, the improvement wherein said pivot means comprises:
   (a) recess means within said base means, said recess means having a concave bearing surface formed as a substantially continuous surface of revolution; and
   (b) said regulating means comprising at least one leaflet having means projecting from the edge thereof and extending into said recess means, said projecting means engaging said concave bearing surface and being formed as a surface of revolution means about an axis normal to the plane of said leaflet and compatible with said concave bearing surface and to wipe the bearing surface and flush the recess means on movement of the regulating means between said open and closed positions.

5. The prosthesis of claim 4 wherein said concave bearing surface and the termini of said projecting means are spherical.

6. The prosthesis of claim 4 wherein an edge surface of said recess means further comprises stop means defining at least one of said regulating means open and closed positions.

7. The prosthesis of claim 6 wherein said concave bearing surface and the termini of said projecting means are spherical.

8. The prosthesis of claim 4 wherein said base means, regulating means and pivot means are each formed of a substrate coated in their entirety with pyrolytic carbon.

9. The prosthesis of claim 8 wherein said concave bearing surface and the termini of said projecting means are spherical.

10. In a heart valve prosthesis of the type having base means including a blood passageway, means for regulating the flow of blood through the passageway and pivot means for maintaining the regulating means in operative relation to the passageway while allowing the regulating means to pivot, under the influence of the blood flow in said passageway, between open and closed positions, the improvement wherein said pivot means comprises:
   (a) recess means within said base means, said recess means having a bearing surface formed as a spherical polygon; and
   (b) means projecting from said regulating means into said recess means, the termini of said projecting means engaging said bearing surface and being configured to wipe the bearing surface and flush the recess means on movement of the regulating means between said open and closed positions.

11. In a heart valve prosthesis of the type having base means including a blood passageway, means for regulating the flow of blood through the passageway and pivot means for maintaining the regulating means in operative relation to the passageway while allowing the regulating means to pivot, under the influence of the blood flow in said passageway, between open and closed positions, the improvement wherein said pivot means comprises:

(a) recess means within said base means, said recess means having a bearing surface formed as a spherical polygon, said recess means further comprising stop means defining at least one of said regulating means open and closed positions; and (b) means projecting from said regulating means into said recess means, the termini of said projecting means engaging said bearing surface and being configured to wipe the bearing surface and flush the recess means on movement of the regulating means between said open and closed positions.

12. In a heart valve prosthesis of the type having base means including a blood passageway, means for regulating the flow of blood through the passageway and pivot means for maintaining the regulating means in operative relation to the passageway while allowing the regulating means to pivot, under the influence of the blood flow in said passageway, between open and closed positions, the improvement wherein said pivot means comprises:

(a) recess means within said base means, said recess means having a bearing surface formed as a spherical polygon; and (b) means projecting from said regulating means into said recess means, the termini of said projecting means engaging said bearing surface and being configured to wipe the bearing surface and flush the recess means on movement of the regulating means between said open and closed positions, said projecting means termini being a spherical polygon.

13. In a heart valve prosthesis of the type having base means including a blood passageway, means for regulating the flow of blood through the passageway and pivot means for maintaining the regulating means in operative relation to the passageway while allowing the regulating means to pivot, under the influence of the blood flow in said passageway, between open and closed positions, the improvement wherein said pivot means comprises:

(a) recess means within said base means, said recess means having a bearing surface formed as a surface of revolution;

(b) said base means further comprising a first generally annular portion and second and third portions in opposing relation to each other and projecting from said first portion in the upstream direction, said second and third portions having flat inner faces and said recess means being within said faces; and (c) means projecting from said regulating means into said recess means, the termini of said projecting means engaging said bearing surface and being configured to wipe the bearing surface and flush the recess means on movement of the regulating means between said open and closed positions.

14. The prosthesis of claim 13 wherein said regulating means comprises first and second occluder means each movable between open and closed positions.

15. The prosthesis of claim 14 wherein said second and third base means portions shield said occluder means when said occluder means are in the closed position.

16. The prosthesis of claim 15 wherein said bearing surface and said projecting means termini are spherical polygons.

* * * * *